United States Patent [19]

Homann et al.

[11] Patent Number: 5,618,707

[45] Date of Patent: Apr. 8, 1997

[54] STEREOSELECTIVE MICROBIAL REDUCTION OF 5-FLUOROPHENYL-5-OXO-PENTANOIC ACID AND A PHENYLOXAZOLIDINONE CONDENSATION PRODUCT THEREOF

[75] Inventors: Michael J. Homann, Clinton; Edward Previte, N. Brunswick, both of N.J.

[73] Assignee: Schering Corporation, Kenilworth, N.J.

[21] Appl. No.: 583,166

[22] Filed: Jan. 4, 1996

[51] Int. Cl.$^6$ .............................. C12P 7/42; C12P 17/14
[52] U.S. Cl. ...................... 435/146; 435/120; 435/280
[58] Field of Search .......................... 435/146, 135, 435/136, 147, 120, 280

[56] References Cited

U.S. PATENT DOCUMENTS

| | | | |
|---|---|---|---|
| 4,879,233 | 11/1989 | Charney | 435/254 |
| 5,371,014 | 12/1994 | Matsuyama et al. | 435/280 |

OTHER PUBLICATIONS

Page entitled "Biological Reductions" information presented at a meeting Oct. 1994.

Page entitled "Ketone Substrates" information presented at a meeting Oct. 1994.

Page entitled "Cultures to screen for carbonyl reduction" information presented at a meeting Sep. 28, 1995.

Page entitled "Summary of selected microbes and growth media, etc...." information presented at a meeting Sep. 28, 1995.

Page entitled "Substrate specificity of alcohol dehydrogenase from *Hansenula subellicosa*" information presented at a meeting Sep. 28, 1995.

Page entitled "Symposium Programme" which lists Sep. 28, 1995 presentation by Dr. David R Dodds (No Publication Date).

*Primary Examiner*—Michael G. Wityshyn
*Assistant Examiner*—S. Saucier
*Attorney, Agent, or Firm*—John J. Maitner; Matthew Boxer

[57] ABSTRACT

A stereoselective reduction of compound II to compound of formula I

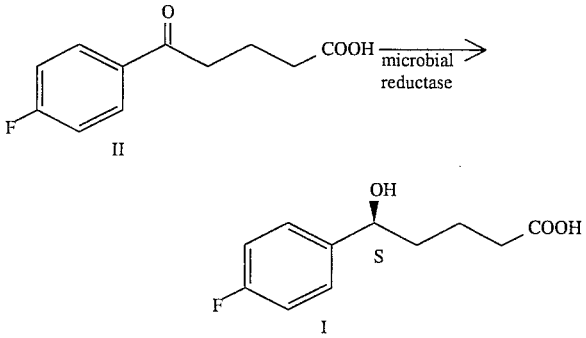

which comprises adding ketone substrate II to a culture broth of the *Zygosaccharomyces bailii* ATCC 38924, incubating the resulting mixture, and isolating a hydroxy compound of formula I, is described. The resulting compound of formula I is useful as an intermediate in the preparation of 1-(4-fluorophenyl)-3(R)-[3(S)-hydroxy-3-(4-fluorophenyl)-propyl]-4(S)-(4-hydroxyphenyl)-2-azetidinone which is a serum cholesterol lowering agent. Also described is a stereoselective reduction of a compound of formula IV to compound of formula III

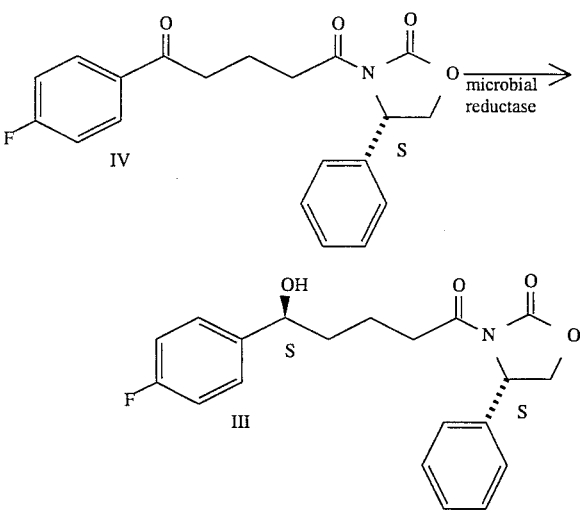

using *Schizosaccharomyces octosporus* ATCC 2479.

2 Claims, No Drawings

STEREOSELECTIVE MICROBIAL REDUCTION OF 5-FLUOROPHENYL-5-OXO-PENTANOIC ACID AND A PHENYLOXAZOLIDINONE CONDENSATION PRODUCT THEREOF

BRIEF SUMMARY OF THE INVENTION

The present invention relates to microbiological reduction of carbonyl groups which comprises cultivating the microorganism *Zygosaccharomyces bailii* American Type Culture Collection (ATCC) 38924, which can be obtained from the American Type Culture Collection, in a medium to which the ketone compound, 4-(4-Fluorobenzoyl)butyric acid (also referred to here as FBBA) can be added so that a compound having a hydroxy group of desired stereochemistry can be formed and accumulated in said medium, and isolating said hydroxy compound. The resulting hydroxy compound, (S)-5-(4-fluorophenyl)hydroxyvaleric acid (FPHVA), is useful as an intermediate in the preparation of 1-(4-fluorophenyl)-3(R)-[3(S)-hydroxy-3-(4-fluorophenyl)propyl]-4(S)-(4-hydroxyphenyl)-2-azetidinone which is a serum cholesterol lowering agent. More specifically, the hydroxy and acid groups of the hydroxy intermediate, FPHVA, can be protected by protecting group chemistry such as that set forth in *Protective Groups in Organic Chemistry*, T. W. Greene, John Wiley & Sons (1981) which is hereby incorporated by reference. The resulting compound is encompassed by formula III set forth at page 8, line 18 of PCT/US94/10099 published 30 Mar. 1995, which is hereby incorporated by reference. PCT/US94/10099 shows the protected form of FPHVA as being converted to the serum cholesterol lowering agent, mentioned above.

DETAILED DESCRIPTION OF THE INVENTION

As noted above, this invention relates to a method for carrying out the following stereospecific microbial reduction:

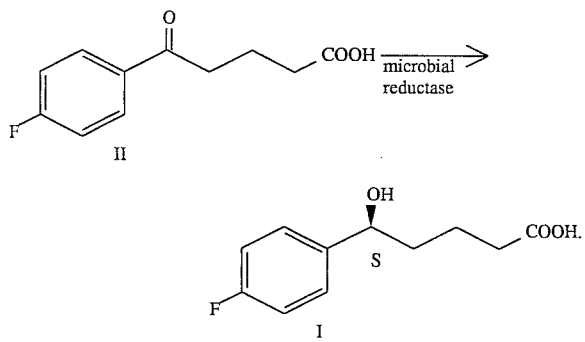

The microbiological chiral reduction is carried out by adding the ketone substrate FBBA (the compound of formula II above) the compound of formula II, to the culture broth of the microorganism. The incubation may be conducted at temperatures in the range from between about 20° C. and about 40° C., and is preferably conducted at 30° C., while adjusting the initial pH value of the reaction mixture in the range from between about 4.0 and about 8.0 preferably 5.5.

The initial concentration of FBBA in the reaction may vary from between about 1.0 g/l and about 20.0 g/l and is preferably 10.0 g/l.

The duration of the chiral reduction reaction may vary from about 18 to about 72 hours, and is preferably about 24–48 hours.

At the end of the reduction reaction, there may be extracted FPHVA, the hydroxy compound of formula I, as described above by using organic solvents such as ethyl acetate, t-butyl methyl ether (TBME), methylene chloride and the like. Adsorption to resins, chromatography and other physical methods known to the art may also be used to extract the FPHVA.

A large number of microorganisms were investigated to determine whether they reduce of the ketone group of FBBA. Many such microorganisms failed to reduce the ketone group of FBBA with the desired specificity or productivity. Of those that did provide the desired specificity or productivity for this reduction, *Zygosaccharomyces bailii* ATCC No. 38924, afforded the highest yields of FPHVA at the highest starting concentration of the ketone, FBBA. This is very desirable, since carrying out this reaction at the highest starting concentration of the ketone, FBBA, affords the most economical means of obtaining the desired ketone, FPHVA.

In the examples below are given the following:

1. A means for identifying the stereoselective microbial reduction of FBBA by *Zygosaccharomyces bailii* ATCC No. 38924, 2. A means for determining that the stereoselective microbial reduction of FBBA by *Zygosaccharomyces bailii* ATCC No. 38924, can be carried out at greater concentrations of FBBA than in the original identification example.

3. A means for carrying out the stereoselective microbial reduction of FBBA by *Zygosaccharomyces bailii* ATCC No. 38924, as flask fermentations 4. A means for carrying out the stereoselective microbial reduction of FBBA by *Zygosaccharomyces bailii* ATCC No. 38924, so as to obtain gram quantities of of the hydroxy compound.

5. A means for carrying out the stereoselective microbial reduction of FBBA by *Zygosaccharomyces bailii* ATCC 38924, as 10-liter flask fermentations

EXAMPLE 1

The general method for identifying the stereoselective microbial reduction of 4-(4-Fluorobenzoyl)butyric acid (FBBA) for use as a synthetic precursor for the production of 1-(4-fluorophenyl)-3(R)-[3(S)-hydroxy-3-(4-fluorophenyl)propyl]-4(S)-(4-hydroxyphenyl)-2-azetidinone is described below.

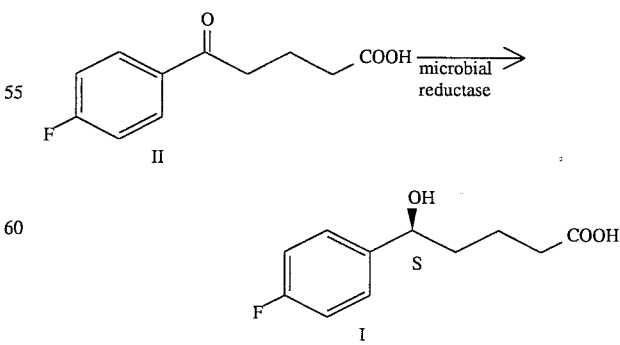

Seed cultures of yeast, filamentous fungi, and bacteria were grown in YPD (1% yeast extract, 2% peptone, 2% dextrose;

pH 5.5), SIM6 (3.5% soy flour, 5% white potato dextrose, 0.5% cerelose, 2 mg/l cobalt chloride, 0.5% calcium carbonate; pH 6.0) and NYC (0.8% nutrient broth, 2% yeast extract, 2% cerelose; pH 7.0) media respectively, for 72 hours at 30° C. with agitation (175–250 rpm) prior to inoculation (4% v/v) into flask fermentations (25 ml YPD/ 125 ml flask for yeast and filamentous fungi or 25 ml NYC/125 ml flask for bacteria) which were incubated at 30 C. with agitation (250 rpm). In all fermentations, medium pH was adjusted prior to inoculation but was not controlled during culture propagation and biotransformation. Bioconversions were initiated by adding substrate (1 g/l) dissolved in methanol (100 mg/ml) directly to cultures following 24 hours of growth. Samples of fermentation broth extracted with TBME (1:2) following 24–48 hours incubation with substrate were analyzed by reverse-phase HPLC. The culture demonstrated consistent reduction activity without significant substrate degradation following repeated fermentations using this procedure, and was further analyzed by chiral HPLC to determine the configuration of the product alcohol. The results from the chiral analysis are summarized in Table 1. The culture exclusively produced the S enantiomer.

TABLE 1

Stereoselective reduction of FBBA (1 g/l) by Z. bailii ATCC 38924 in flask fermentation.

| Culture | % Alcohol | % EE (Configuration) |
|---|---|---|
| Zygosaccharomyces bailii ATCC 38924 | 68 | 100 (S) |

EXAMPLE 2

The general method for determining that Z. bailii ATCC 38924 is capable of reducing FBBA at concentrations greater than those used in Example 1 is described below.

Seed cultures of yeast were grown in YPD medium (1% yeast extract, 2% peptone, 2% dextrose; pH 5.5) for 72 hours at 30° C. with agitation (250 rpm) prior to inoculation (4% v/v) into flask fermentations (25 ml YPD/125 ml flask) incubated at 30° C. with agitation (250 rpm). In all fermentations, medium pH was adjusted prior to inoculation but was not controlled during culture propagation and biotransformation. Bioconversions were initiated by adding substrate (1–4 g/l) dissolved in methanol (100 mg/ml) directly to cultures at inoculation, following 24 hours of growth or both as indicated in Table 2. Samples of fermentation broth extracted with TBME (1:2) following 24–48 hours incubation with substrate were analyzed by reverse-phase HPLC. The utility of this reduction may be diminished by large amounts of lactone formed by intramolecular condensation between the alcohol and carboxylic acid chemical groups. Thus, the HPLC analysis was specifically designed to detect the presence of lactone. The results of this analysis are summarized in Table 2.

TABLE 2

Reduction of FBBA (1–4 g/l) by Z. bailii in flask fermentations.

| Culture | Substrate Conc./Addition Time | % Ketone | % Alcohol | % Lactone |
|---|---|---|---|---|
| Zygosaccharomyces bailii 38924 | 1 g/l at log 24 | 4 | 96 | 0 |
| | 1 g/l at logs 0 + 24 | 0 | 100 | 0 |
| | 4 g/l at log 24 | 43 | 57 | 0 |

EXAMPLE 3

The general method for investigating the fermentation parameters for the reduction of FBBA by Z. bailii ATCC 38924 in flask fermentations is described below.

Seed cultures of Z. bailii ATCC38924 were grown in YPD (1% yeast extract, 2% peptone, 2% dextrose; pH 5.5) or TNC (1% Tastone 154, 2% NZ amine, 3% cerelose; pH 5.5) for 24–72 hours at 30 C. with agitation (250 rpm) prior to inoculation (2–8% v/v) into flask fermentations (25 ml–100 ml/125–300 ml flask) which were incubated at 30 C. with agitation (250 rpm) where indicated in Table 3. In all fermentations, medium pH was adjusted prior to inoculation but was not controlled during culture propagation and biotransformation. Bioconversions were initiated by adding substrate (4–10 g/l) dissolved in methanol (MeOH; 100 mg/ml) or dimethylsulfoxide (DMSO; 500 mg/ml with slight heat) directly to cultures following 24 hours of growth. Samples of fermentation broth were taken following 24–72 hours of incubation with substrate and extracted with TBME (1:4). Extracts were diluted with ethanol (1:1) prior to analysis by reverse-phase HPLC. The results of this analysis are summarized in Table 3. Complete reduction of 10 g/l substrate was achieved within 72 hours, using a fed batch fermentation employing TNC medium (1% Tastone 154, 2% NZ amine, 3% cerelose) and feeding cerelose (3%) 24 hours following substrate addition (parameter set #31). Conversion yields as high as 95% could also be achieved using medium containing 6% cerelose at inoculation (parameter set #30).

TABLE 3

Reduction of FBBA (4–10 g/l) by Z. bailii ATCC 38924 in flask fermentations.

| Parameter Set # | Seed Conditions | Seed Age (hour) | Transfer Vol. (% v/v) | Bio-conversion, Conditions | Substrate (g/l) | Solvent | % Alcohol |
|---|---|---|---|---|---|---|---|
| 1 | YPD | 24 | 2 | YPD | 4 | MeOH | 55 |
| 2 | 25 ml/125 ml | 24 | 4 | 25 ml/125 ml | 4 | | 41 |
| 3 | 250 rpm, 30 C. | 24 | 8 | 250 rpm, 30 C. | 4 | | 36 |
| 1a | YPD | 24 | 2 | YPD | 5 | MeOH | 37 |
| 1b | 25 ml/125 ml | 24 | 4 | 25 ml/125 ml | 5 | | 34 |
| 1c | 250 rpm, 30 C. | 24 | 8 | 250 rpm, 30 C. | 5 | | 33 |
| 4 | YPD | 48 | 2 | YPD | 4 | MeOH | 48 |
| 5 | 25 ml/125 ml | 48 | 4 | 25 ml/125 ml | 4 | | 47 |
| 6 | 250 rpm, 30 C. | 48 | 8 | 250 rpm, 30 C. | 4 | | 32 |

TABLE 3-continued

Reduction of FBBA (4–10 g/l) by *Z. bailii* ATCC 38924 in flask fermentations.

| Parameter Set # | Seed Conditions | Seed Age (hour) | Transfer Vol. (% v/v) | Bio-conversion, Conditions | Substrate .(g/l) | Solvent | % Alcohol |
|---|---|---|---|---|---|---|---|
| 4a | YPD | 48 | 2 | YPD | 5 | MeOH | 43 |
| 5a | 25 ml/125 ml | 48 | 4 | 25 ml/125 ml | 5 | | 33 |
| 6a | 250 rpm, 30 C. | 48 | 8 | 250 rpm, 30 C. | 5 | | 28 |
| 7 | YPD | 72 | 2 | YPD | 4 | MeOH | 72 |
| 8 | 25 ml/125 ml | 72 | 4 | 25 ml/125 ml | 4 | | 57 |
| 9 | 250 ml/125 ml | 72 | 8 | 250 rpm, 30 C. | 4 | | 56 |
| 7a | YPD | 72 | 2 | YPD | 5 | MeOH | 48 |
| 8a | 25 ml/125 ml | 72 | 4 | 25 ml/125 ml | 5 | | 42 |
| 9a | 250 rpm, 30 C. | 72 | 8 | 250 rpm, 30 C. | 5 | | 39 |
| 10 | YPD | 24 | 4 | YPD | 4 | MeOH | 95 |
| 11 | 25 ml/125 ml | 48 | 4 | 50 ml/300 ml | 4 | | 48 |
| 12 | 250 rpm, 30 C. | 72 | 4 | 250 rpm, 30 C. | 4 | | 72 |
| 10a | YPD | 24 | 4 | YPD | 5 | MeOH | 46 |
| 11a | 25 ml/125 ml | 48 | 4 | 50 ml/300 ml | 5 | | 40 |
| 12a | 250 rpm, 30 C. | 72 | 4 | 250 rpm, 30 C. | 5 | | 57 |
| 13 | YPD | 24 | 4 | YPD | 4 | MeOH | 33 |
| 14 | 25 ml/125 ml | 48 | 4 | 30 ml/300 ml | 4 | | 36 |
| 15 | 250 rpm, 30 C. | 72 | 4 | 250 rpm, 30 C. | 4 | | 42 |
| 13a | YPD | 24 | 4 | YPD | 5 | MeOH | 22 |
| 14a | 25 ml/125 ml | 48 | 4 | 30 ml/300 ml | 5 | | 26 |
| 15a | 250 rpm, 30 C. | 72 | 4 | 250 rpm, 30 C. | 5 | | 31 |
| 16 | YPD | 24 | 4 | YPD | 4 | MeOH | 11 |
| 17 | 25 ml/125 ml | 48 | 4 | 50 ml/300 ml | 4 | | 10 |
| 18 | 250 rpm, 30 C. | 72 | 4 | Baffled 175 rpm, 30 C. | 4 | | 19 |
| 16a | YPD | 24 | 4 | YPD | 5 | MeOH | 11 |
| 17a | 25 ml/125 ml | 48 | 4 | 50 ml/300 ml | 5 | | 10 |
| 18a | 250 rpm, 30 C. | 72 | 4 | Baffled 175 rpm, 30 C. | 5 | | 13 |
| 19 | YPD | 24 | 4 | YPD | 4 | MeOH | 100 |
| 20 | 25 ml/125 ml | 48 | 4 | 100 ml/300 ml | 4 | | 100 |
| 21 | 250 rpm, 30 C. | 72 | 4 | 250 rpm, 30 C. | 4 | | 121 |
| 19a | YPD | 24 | 4 | YPD | 5 | MeOH | 91 |
| 20a | 25 ml/125 ml | 48 | 4 | 100 ml/300 ml | 5 | | 84 |
| 21a | 250 rpm, 30 C. | 72 | 4 | 250 rpm, 30 C. | 5 | | 100 |
| 22 | TNC | 72 | 2 | TNC | 4 | MeOH | 99 |
| 23 | 25 ml/125 ml | 72 | 4 | 100 ml/300 ml | 4 | | 99 |
| 24 | 250 rpm, 30 C. | 72 | 2 | 250 rpm, 30 C. | 6 | | 94 |
| 25 | | 72 | 4 | | 6 | | 88 |
| 22a | TNC | 72 | 2 | TNC | 5 | MeOH | 100 |
| 23a | 25 ml/125 ml | 72 | 4 | 100 ml/300 ml | 5 | | 90 |
| 24a | 250 rpm, 30 C. | 72 | 2 | 250 rpm, 30 C. | 8 | | 39 |
| 25a | | | 4 | | 8 | | 62 |
| 26 | TNC | 72 | 2 | TNC | 6 | MeOH | 1 |
| 27 | 25 ml/125 ml 250 rpm, 30 C. | 72 | 4 | 100 ml/300 ml 250 rpm, 34 C. | 6 | | 2 |
| 26a | TNC | 72 | 2 | TNC | 8 | MeOH | 0 |
| 27a | 25 ml/125 ml 250 rpm, 30 C. | 72 | 4 | 100 ml/300 ml 250 rpm, 34 C. | 8 | | 1 |
| 28 | TNC 100 ml/300 ml 250 rpm, 30 C. | 72 | 4 | TNC 100 ml/300 ml 250 rpm, 30 C. | 6 | MeOH | 85 |
| 28a | TNC 100 ml/300 ml 250 rpm, 30 C. | 72 | 4 | TNC 100 ml/300 ml 250 rpm, 30 C. | 8 | MeOH | 50 |
| 29 | TNC | 72 | 4 | TNC | 8 | DMSO | 78 |
| 30 | 100 ml/300 ml | 72 | 4 | TN2C | 10 | | 82–95 |
| 31 | 250 rpm, 30 C. | 72 | 4 | TNC + 3% cerelose (24 h post subst.) 100 ml/300 ml 250 rpm, 30 C. | 10 | | 100 |
| 29a | TNC 100 ml/300 ml 250 rpm, 30 C. | 72 | 4 | TNC TN2C TNC + 3% cerelose (24 h post subst.) 100 ml/300 ml 250 rpm, 30 C. | 10 | DMSO | 76 |

EXAMPLE 4

Gram quantities of FPHVA derived from the stereoselective reduction of FBBA were prepared using *Z. bailii* ATCC 38924 and isolated in the following manner.

Seed cultures were grown in YPD medium (25 ml/125 ml flask) for 72 hours at 30 C. with agitation prior to inoculation (4% v/v) into flask fermentations (80×25 ml/125 ml flask). Medium pH was adjusted prior to inoculation but was not controlled during culture propagation and biotransformation. Bioconversions were initiated by adding substrate (4 g/l) dissolved in methanol (100 mg/ml) directly to cultures following 24 hours of growth and incubated 24 hours at 30 C. with agitation (250 rpm). Pooled fermentation broth (2 L) was centrifuged to remove cells and the supernatant (1.87 L) extracted with methyl tert-butyl ether (1:0.5). Anhydrous magnesium sulfate was added to the solvent extract to remove residual water and removed by filtration. The filtrate was concentrated by evaporation and subjected to purification by silica gel chromatography (2×10 inch column bed). Material was eluted from the column with a solution of methylene chloride:ethyl acetate (60:40). Peak fractions containing only hydroxy acid product were identified by thin layer chromatography, pooled and concentrated by evaporation. A total of 1.2 g of the reduced product was isolated with a purity of 99.8% (100% S) with no detectable levels of lactone as detected by reverse phase and chiral HPLC. Samples of this material were confirmed to be the desired product by NMR, mass spectrum and elemental analyses.

EXAMPLE 5

The general method for the bioconversion of FBBA to FPHVA using *Z. bailii* ATCC 38924 in 10 liter fermentors is described below.

First stage seed cultures were grown in TNC medium (1% Tastone 154, 2% NZ amine, 3% cerelose; pH 5.5) using 100 ml/300 ml flasks for 60–72 hours at 30 C. with agitation (250 rpm) prior to serial transfer (5%) into second stage seed fermentations employing TNC medium (500 ml/2 L flask) incubated at 30 C. with agitation (200 rpm). Following 24 hours of growth, second stage seed cultures were used to inoculate (5% v/v) fermentors containing 5–10 liters of TN2C medium (1% Tastone 154, 2% NZ amine, 6% cerelose; pH 5.5). The culture was propagated in the fermentor at 30 C., with agitation (impellor speed; 600 rpm) and aeration (airflow; 3–10 lpm) under pressure (5 psi). Dissolved oxygen was maintained at or above 30% by adjusting agitation speed and aeration rates. Culture growth was monitored by analyzing off gas for carbon dioxide and medium pH was adjusted prior to inoculation but was not controlled during culture propagation and biotransformation. Bioconversions were initiated by adding substrate (10 g/l) dissolved in dimethyl sulfoxide (400 mg/ml) directly to cultures when the off gas attained an initial concentration of 3.9%. Additional cerelose (3% w/v) was added to the ongoing fermentation following maximum carbon dioxide evolution, when the off gas contained 2% carbon dioxide. Samples of fermentation broth were taken following 24–72 hours of incubation with substrate and extracted with TBME (1:4). Extracts were diluted with ethanol (1:1) prior to analysis by reverse-phase HPLC. Approximately 85% of the substrate was reduced following 48 hours of incubation.

EXAMPLE 6

Reduction of FBBA-phenyloxazolidinone Conjugate by Selected Microbes

The general method for identifying the stereoselective microbial reduction of the condensation product formed from 4-(4-Fluorobenzoyl)butyric acid (FBBA) and phenyloxazoliclinone for use as a synthetic precursor for the production of 1-(4-fluorophenyl)-3(R)-[3(S)-hydroxy-3-(4-fluorophenyl)propyl)]-4(S)-(4-hydroxyphenyl)-2-azetidinone is described below.

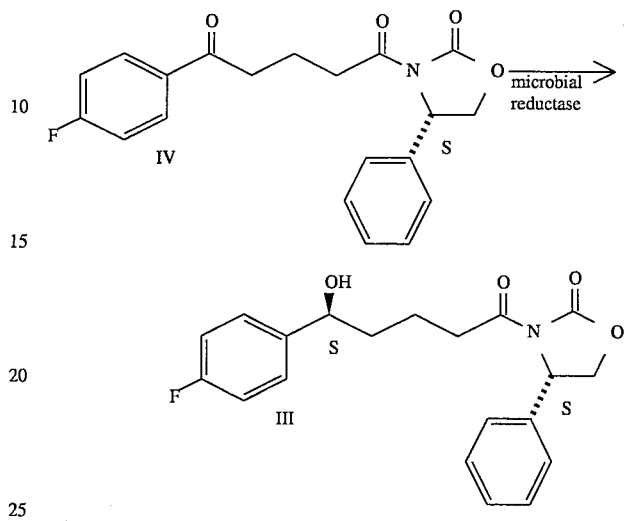

Seed cultures of yeast, filamentous fungi, and bacteria were grown in YPD (1% yeast extract, 2% peptone, 2% dextrose; pH 5.5), SIM6 (3.5% soy flour, 5% white potato dextrose, 0.5% cerelose, 2 mg/l cobalt chloride, 0.5% calcium carbonate; pH 6.0) and NYC (0..8% nutrient broth, 2% yeast extract, 2% cerelose; pH7.0) media respectively, for 72 hours at 30 C. with agitation (175–250 rpm) prior to inoculation (4% v/v) into flask fermentations (25 ml YPD/125 ml flask for yeast and filamentous fungi or 25 ml NYC/125 ml flask for bacteria) incubated at 30 C. with agitation (250 rpm). In all fermentations, medium pH was adjusted prior to inoculation but was not controlled during culture propagation and biotransformation. Bioconversions were initiated by adding substrate (1 g/l) dissolved in methanol (100 mg/ml) directly to cultures following 24 hours of growth. Product synthesis and stereoselectivity were determined by chiral HPLC using samples of fermentation broth extracted with TBME (1:2) following 24–48 hours incubation with substrate. The cultures identified in this manner as being capable of reducing FBBA-phenyloxazolidinone are summarized in Table 4.

Multiple flask bioconversions were conducted employing *S. octosporus* ATCC 2479 to generate material for chemical characterization. Seed cultures were grown in YPD medium (25 ml/125 ml flask) for 72 hours at 30 C. with agitation prior to inoculation (4% v/v) into flask fermentations (20× 100 ml/300 ml). Medium pH was adjusted prior to inoculation but was not controlled during culture propagation and biotransformation. Substrate addition (1 g/l dissolved in methanol at 100 mg/ml) to flask fermentations following 24 hours of growth at 30 C. with agitation (250 rpm), provided the best conversion with product yields as high as 35%. Pooled fermentation broth was centrifuged to remove cells and the supernatant extracted with ethyl acetate (1:0.5). The extract was washed twice with an equal volume of salt solution (6M sodium chloride) followed by deionized distilled water. Anhydrous magnesium sulfate was added to the ethyl acetate extract to remove residual water, the extract was filtered and the filtrate concentrated by evaporation. Extract concentrate was subjected to purification by silica gel chromatography (1×12 inch column bed). Material was eluted from the column with a solution of methylene chloride:ethyl acetate:acetic acid (90:10:0.5). Peak fractions containing products were pooled and concentrated by evaporation, followed by separation on preparative thin layer chromatography plates employing a solution of ethyl acetate:hexane:acetic acid (60:40:0.5). Two products were isolated from the bioconversion using this procedure and shown to be the desired reduced alcohol conjugate and the phenyloxazolidinone reagent as determined by HPLC and NMR analyses.

TABLE 4

Reduction of FBBA-phenyloxazolidinone conjugate by *Schizosaccharomyces octosporus*

| Culture | ATCC # | Remaining Substrate (%) | Product Yield (%) | DE (% SS/% |
|---|---|---|---|---|
| Schizosaccharomyces octosporus | 2479 | 67 | 33 | 100 SS |
| | 4206 | 36 | 34 | 100 SS |

What is claimed is:

1. A stereoselective reduction of a compound of formula II to compound of formula I

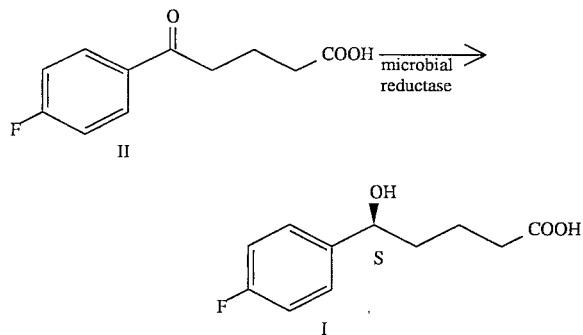

which comprises adding a compound of formula II to a culture broth of *Zygosaccharomyces bailii* ATCC 38924, incubating the resulting mixture, and isolating a hydroxy compound of formula I.

2. A stereoselective reduction of a compound of formula IV to compound of formula III

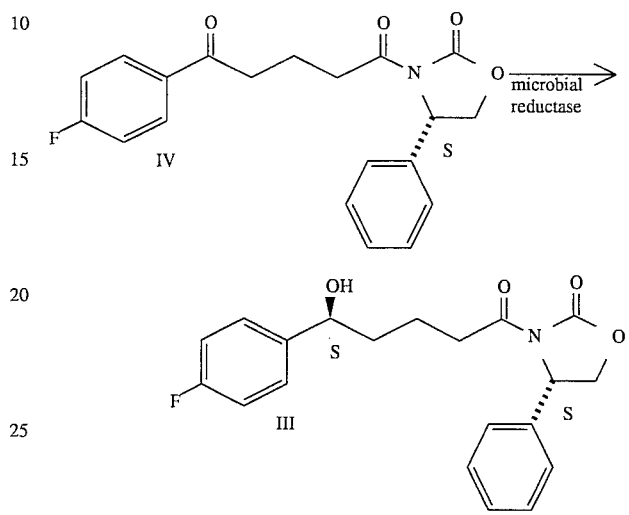

which comprises adding a compound of formula IV to a culture broth of *Schizosaccharomyces octosporus* ATCC 2479, incubating the resulting mixture, and isolating a hydroxy compound of formula III.

* * * * *